(12) United States Patent
Wang

(10) Patent No.: US 11,276,793 B2
(45) Date of Patent: Mar. 15, 2022

(54) SEMICONDUCTOR DEVICE

(71) Applicant: VisEra Technologies Company Limited, Hsin-Chu (TW)

(72) Inventor: Wei-Ko Wang, Taoyuan (TW)

(73) Assignee: VISERA TECHNOLOGIES COMPANY LIMITED, Hsin-Chu (TW)

(*) Notice: Subject to any disclaimer, the term of this patent is extended or adjusted under 35 U.S.C. 154(b) by 0 days.

(21) Appl. No.: 16/892,466

(22) Filed: Jun. 4, 2020

(65) Prior Publication Data

US 2021/0384368 A1   Dec. 9, 2021

(51) Int. Cl.
| | |
|---|---|
| H01L 29/06 | (2006.01) |
| H01L 31/00 | (2006.01) |
| H01L 31/0352 | (2006.01) |
| H01L 31/0216 | (2014.01) |
| H01L 31/02 | (2006.01) |

(52) U.S. Cl.
CPC .. *H01L 31/035281* (2013.01); *H01L 31/0216* (2013.01); *H01L 31/02024* (2013.01)

(58) Field of Classification Search
CPC ....... H01L 31/035281; H01L 31/02024; H01L 31/0216; H01L 31/02165; H01L 31/02164; H01L 31/02327; H01L 27/14678; H01L 27/14625–14629; H01L 27/1463; H01L 51/447; G02B 3/00; G02B 5/00; G02B 6/00
USPC .......................................................... 257/21
See application file for complete search history.

(56) References Cited

U.S. PATENT DOCUMENTS

| | | | |
|---|---|---|---|
| 2012/0068294 | A1 | 3/2012 | Lee et al. |
| 2016/0305820 | A1* | 10/2016 | Zollars .................. G01J 3/2823 |
| 2018/0366501 | A1* | 12/2018 | Asatsuma ......... H01L 27/14623 |
| 2019/0391508 | A1* | 12/2019 | Nakamichi .......... H04N 1/1061 |
| 2020/0127030 | A1* | 4/2020 | Ogawa ................... H04N 5/369 |

FOREIGN PATENT DOCUMENTS

| | | |
|---|---|---|
| CN | 105229787 A | 1/2016 |
| JP | 2004253630 A | 9/2004 |
| JP | 2019135792 A | 8/2019 |
| TW | 202002258 A | 1/2020 |
| WO | WO-2018189613 A1 | 10/2018 |

OTHER PUBLICATIONS

Taiwan Office Action with search report of corresponding TW application No. 109127507 dated Jun. 2, 2021, 4 pages.

* cited by examiner

*Primary Examiner* — Calvin Y Choi
(74) *Attorney, Agent, or Firm* — Muncy, Geissler, Olds & Lowe, P.C.

(57) ABSTRACT

A semiconductor device is provided. The semiconductor device includes a substrate having a photoelectric conversion element, a first light-shielding layer disposed on the substrate and having a first aperture, a light-transmitting layer disposed on the first light-shielding layer, at least one second light-shielding layer disposed in the light-transmitting layer and having a second aperture, and a light-condensing structure disposed on the light-transmitting layer. The orthogonal projection of the second aperture on the bottom surface of the substrate has a long axis of symmetry and a short axis of symmetry perpendicular to the long axis of symmetry.

16 Claims, 4 Drawing Sheets

SEMICONDUCTOR DEVICE

BACKGROUND

Technical Field

Embodiments of the present disclosure relate to a semiconductor device, and in particular they relate to a semiconductor device for receiving/collecting inclined light.

Description of the Related Art

Semiconductor devices may be used in a variety of applications. For example, in recent years, semiconductor devices with photoelectric conversion elements have often been used as biometric devices, such as fingerprint identification devices, facial-recognition devices, iris scanners, and so on. Biometric devices may use people's intrinsic physical characteristics (e.g., a fingerprint, a face, an iris, and so on) to verify their identification, and they are usually used in portable devices (e.g., cell phones, tablet computers, notebooks, and so on). This application of biometric devices brings users a safe and convenient user experience.

However, existing biometric devices have not been satisfactory in every respect. For example, the reflection of the photoelectric conversion element in the biometric device may easily be seen by the user. Inclined system used in the biometric device (i.e., the biometric device is designed for receiving/collecting inclined light) may solve the foregoing problem, but may also cause crosstalk.

BRIEF SUMMARY

In some embodiments of the present disclosure, the semiconductor device includes at least one light-shielding layer disposed in the light-transmitting layer and having an aperture. The aperture has a long axis of symmetry and a short axis of symmetry perpendicular to the long axis of symmetry, which may be used for receiving/collecting inclined light and preventing crosstalk, thereby improving the quality of the image signal from the photoelectric conversion elements of the semiconductor devices.

In accordance with some embodiments of the present disclosure, a semiconductor device is provided. The semiconductor device includes a substrate having a photoelectric conversion element. The semiconductor device also includes a first light-shielding layer disposed on the substrate and having a first aperture corresponding to the photoelectric conversion element. The semiconductor device further includes a light-transmitting layer disposed on the first light-shielding layer. The semiconductor device includes at least one second light-shielding layer disposed in the light-transmitting layer and having a second aperture corresponding to the first aperture. The semiconductor device also includes a light-condensing structure disposed on the light-transmitting layer and corresponding to the second aperture. The orthogonal projection of the second aperture on the bottom surface of the substrate has a long axis of symmetry and a short axis of symmetry perpendicular to the long axis of symmetry.

In some embodiments, the short axis of symmetry is parallel with the connecting line of the center of the orthogonal projection of the first aperture on the bottom surface of the substrate and the center of the orthogonal projection of the light-condensing structure on the bottom surface of the substrate.

In some embodiments, the short axis of symmetry overlaps the connecting line of the center of the orthogonal projection of the first aperture on the bottom surface of the substrate and the center of the orthogonal projection of the light-condensing structure on the bottom surface of the substrate.

In some embodiments, the orthogonal projection of the light-condensing structure on the bottom surface of the substrate is circular.

In some embodiments, the orthogonal projection of the second aperture on the bottom surface of the substrate is ellipsoidal.

In some embodiments, the long axis of symmetry is the major axis of the orthogonal projection of the second aperture and the short axis of symmetry is the minor axis of the orthogonal projection of the second aperture.

In some embodiments, the orthogonal projection of the second aperture on the bottom surface of the substrate is rectangular.

In some embodiments, the orthogonal projection of the light-condensing structure on the bottom surface of the substrate is square-shaped.

In some embodiments, the orthogonal projection of the light-condensing structure on the bottom surface of the substrate is square-shaped, and the orthogonal projection of the second aperture on the bottom surface of the substrate is rectangular.

In some embodiments, the orthogonal projection of the second aperture on the bottom surface of the substrate is polygon-shaped.

In some embodiments, the semiconductor device further includes a third light-shielding layer disposed on the light-transmitting layer and having a third aperture corresponding to the second aperture.

In some embodiments, the light-condensing structure covers the third aperture.

In some embodiments, the third aperture has the same shape as the light-condensing structure.

In some embodiments, the distance between the first light-shielding layer and the at least one second light-shielding layer is different from the distance between the at least one second light-shielding layer and the third light-shielding layer.

In some embodiments, the material of the first light-shielding layer includes a metal.

In some embodiments, the material of the at least one second light-shielding layer includes a photoresist, an ink, a molding compound, a solder mask, an epoxy resin or a combination thereof.

In some embodiments, the light-condensing structure includes a micro-lens structure, a micro-pyramid structure, a micro-trapezoidal structure or a gradient-index structure.

BRIEF DESCRIPTION OF THE DRAWINGS

The disclosure can be more fully understood from the following detailed description when read with the accompanying figures. It is worth noting that, in accordance with standard practice in the industry, various features are not drawn to scale. In fact, the dimensions of the various features may be arbitrarily increased or reduced for clarity of discussion.

DETAILED DESCRIPTION

Figure 1:
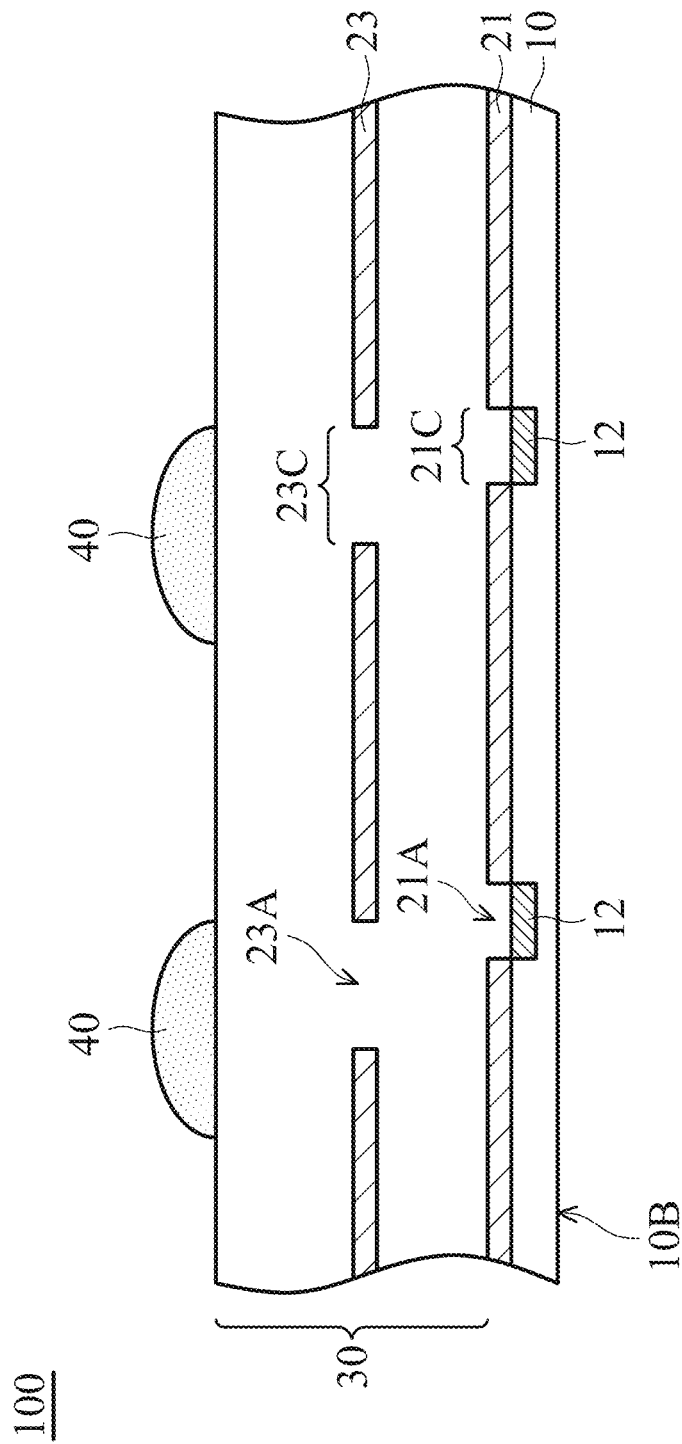
FIG. 1 is a partial cross-sectional view illustrating a semiconductor device according to an embodiment of the present disclosure.

The following disclosure provides many different embodiments, or examples, for implementing different features of the subject matter provided. Specific examples of components and arrangements are described below to simplify the present disclosure. These are, of course, merely examples and are not intended to be limiting. For example, a first feature is formed on a second feature in the description that follows may include embodiments in which the first feature and second feature are formed in direct contact, and may also include embodiments in which additional features may be formed between the first feature and second feature, so that the first feature and second feature may not be in direct contact.

It should be understood that additional steps may be implemented before, during, or after the illustrated methods, and some steps might be replaced or omitted in other embodiments of the illustrated methods.

Furthermore, spatially relative terms, such as "beneath," "below," "lower," "on," "above," "upper" and the like, may be used herein for ease of description to describe one element or feature's relationship to other elements or features as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Unless otherwise defined, all terms (including technical and scientific terms) used herein have the same meaning as commonly understood by one of ordinary skill in the art to which this disclosure belongs. It should be understood that terms such as those defined in commonly used dictionaries should be interpreted as having a meaning that is consistent with their meaning in the context of the relevant art and will not be interpreted in an idealized or overly formal sense unless expressly so defined in the embodiments of the present disclosure.

The present disclosure may repeat reference numerals and/or letters in following embodiments. This repetition is for the purpose of simplicity and clarity and does not in itself dictate a relationship between the various embodiments and/or configurations discussed.

The semiconductor device in the embodiments of the present disclosure may be used as a biometric device, such as a fingerprint identification device, but the present disclosure is not limited thereto. The semiconductor device shown in the embodiments of the present disclosure may also be applied to other suitable devices, depending on requirements.

FIG. 1 is a partial cross-sectional view illustrating a semiconductor device 100 according to an embodiment of the present disclosure. It should be noted that some components of the semiconductor device 100 may be omitted in FIG. 1, for the sake of brevity.

Referring to FIG. 1, the semiconductor device 100 includes a substrate 10. In some embodiments, the material of the substrate 10 may include an elemental semiconductor (e.g., silicon, germanium), a compound semiconductor (e.g., tantalum carbide (TaC), gallium arsenide (GaAs), indium arsenide (InAs) or indium phosphide (InP)), an alloy semiconductor (e.g., silicon germanium (SiGe), silicon germanium carbide (SiGeC), gallium arsenic phosphide (GaAsP) or gallium indium phosphide (GaInP)), any other applicable semiconductor, or a combination thereof, but the present disclosure is not limited thereto.

In some embodiments, the substrate 10 may be a semiconductor-on-insulator (SOI) substrate. For example, the substrate 10 may be a silicon-on-insulator substrate or a germanium-on-insulator substrate, but the present disclosure is not limited thereto. In some embodiments, the substrate 10 may be a semiconductor wafer (e.g., a silicon wafer, or any other applicable semiconductor wafer). In some embodiments, the substrate 10 may include various conductive features (e.g., conductive lines or vias). For example, the conductive features may be made of aluminum (Al), copper (Cu), tungsten (W), an alloy thereof, any other applicable conductive material, or a combination thereof, but the present disclosure is not limited thereto.

As shown in FIG. 1, the substrate 10 may have a plurality of photoelectric conversion elements 12. In some embodiments, the photoelectric conversion elements 12 may be formed by a process such as an ion implantation process and/or a diffusion process. For example, the photoelectric conversion elements 12 may be configured to form transistors, photodiodes, PIN diodes and/or light-emitting diodes, but the present disclosure is not limited thereto. In some embodiments, the photoelectric conversion elements 12 may form an array structure, but the present disclosure is not limited thereto.

Referring to FIG. 1, the semiconductor device 100 includes a first light-shielding layer 21 disposed on the substrate 10. As shown in FIG. 1, the first light-shielding layer 21 may have a plurality of first apertures 21A that correspond to the photoelectric conversion elements 12. In some embodiments, the material of the first light-shielding layer 21 may include a metal, such as tungsten (W), copper (Cu), silver (Ag), and so on, but the present disclosure is not limited thereto. In some other embodiments, the material of the first light-shielding layer 21 may include photoresist (e.g., black photoresist, or other applicable photoresist which is not transparent), ink (e.g., black ink, or other applicable ink which is not transparent), molding compound (e.g., black molding compound, or other applicable molding compound which is not transparent), solder mask (e.g., black solder mask, or other applicable solder mask which is not transparent), (black-)epoxy polymer, any other applicable material, or a combination thereof. In some embodiments, the material of the first light-shielding layer 21 may include a light curing material, a thermal curing material, or a combination thereof.

In some embodiments, the material of the first light-shielding layer 21 may be deposited on the substrate 10 by a deposition process, such as physical vapor deposition (PVD), chemical vapor deposition (CVD), atomic layer deposition (ALD), molecular beam epitaxy (MBE), liquid phase epitaxy (LPE), the like, or a combination thereof, but the present disclosure is not limited thereto. Then, a patterning process may be performed to pattern the material of the first light-shielding layer 21 and form the first apertures 21A as shown in FIG. 1. In more detail, some portions of the material of the first light-shielding layer 21 may be removed in the patterning process to form the first apertures 21A. In some embodiments, the patterning process may include soft baking, mask aligning, exposure, post-exposure baking, developing, rinsing, drying, any other applicable process, or a combination thereof, but the present disclosure is not limited thereto.

Referring to FIG. 1, the semiconductor device 100 includes a light-transmitting layer 30 disposed on the first light-shielding layer 21. In more detail, the light-transmitting layer 30 may also be filled in the first apertures 21A of the first light-shielding layer 21 and disposed on the photoelectric conversion elements 12 as shown in FIG. 1. In some embodiments, the material of the light-transmitting layer 30 may include transparent photoresist, polyimide, epoxy resin, any other applicable material, or a combination thereof, but the present disclosure is not limited thereto. In some embodiments, the material of the light-transmitting layer 30 may include a light curing material, a thermal curing material, or a combination thereof. For example, a spin-on coating process may be performed to coat the material of the light-transmitting layer 30 on the first light-shielding layer 21 (in the first apertures 21A) and the photoelectric conversion elements 12 to form the light-transmitting layer 30, but the present disclosure is not limited thereto.

Referring to FIG. 1, the semiconductor device 100 includes at least one second light-shielding layer 23 disposed in the light-transmitting layer 30. As shown in FIG. 1, the second light-shielding layer 23 may have a plurality of second apertures 23A that correspond to the first apertures 21A and photoelectric conversion elements 12. In some embodiments, the cross-sectional area 23C of the second aperture 23A is different from the cross-sectional area 21C of the first aperture 21A. For example, the cross-sectional area 23C of the second aperture 23A may be larger than the cross-sectional area 21C of the first aperture 21A, but the present disclosure is not limited thereto.

In some embodiments, the material of the second light-shielding layer 23 may include photoresist (e.g., black photoresist, or other applicable photoresist which is not transparent), ink (e.g., black ink, or other applicable ink which is not transparent), molding compound (e.g., black molding compound, or other applicable molding compound which is not transparent), solder mask (e.g., black solder mask, or other applicable solder mask which is not transparent), (black-)epoxy polymer, any other applicable material, or a combination thereof. In some embodiments, the material of the second light-shielding layer 23 may include a light curing material, a thermal curing material, or a combination thereof.

In some embodiments, a portion of the light-transmitting layer 30 is formed before forming the second light-shielding layer 23. Then, the material of the second light-shielding layer 23 may be deposited and patterned on the portion of the light-transmitting layer 30 by a deposition process and a patterning process. Examples of the deposition process and the patterning process are as described above, and will not be repeated here. Then, another portion of the light-transmitting layer 30 is formed on the second light-shielding layer 23 and filled in the second apertures 23A, so that the second light-shielding layer 23 may be disposed in the light-transmitting layer 30, but the present disclosure is not limited thereto.

Referring to FIG. 1, the semiconductor device 100 includes a plurality of light-condensing structures 40 disposed on the light-transmitting layer 30. As shown in FIG. 1, the light-condensing structures 40 may correspond to the second apertures 23A, the first aperture 21A, and the photoelectric conversion elements 12. In some embodiments, the light-condensing structures 40 may include micro-lens structures, but the present disclosure is not limited thereto. In some other embodiments, the light-condensing structures 40 may include micro-pyramid structures, micro-trapezoidal structures or gradient-index structures.

In some embodiments, the semiconductor device 100 may be referred to as an inclined system. That is, the semiconductor device 100 may be used for receiving/collecting inclined light (e.g., light with an incident angle between 30 and 50 degrees), so that the reflection of the photoelectric conversion elements 12 in the semiconductor device (biometric device) 100 may not easily be seen by the user.

Moreover, the shape of the second aperture 23A of the second light-shielding layer 23 in the semiconductor device 100 may be different compared to the general aperture in the traditional semiconductor device (biometric device). In some embodiments of the present disclosure, the second aperture 23A may have a long axis of symmetry and a short axis of symmetry perpendicular to the long axis of symmetry, which will be described in more detail referring to FIG. 2.

Figure 2:
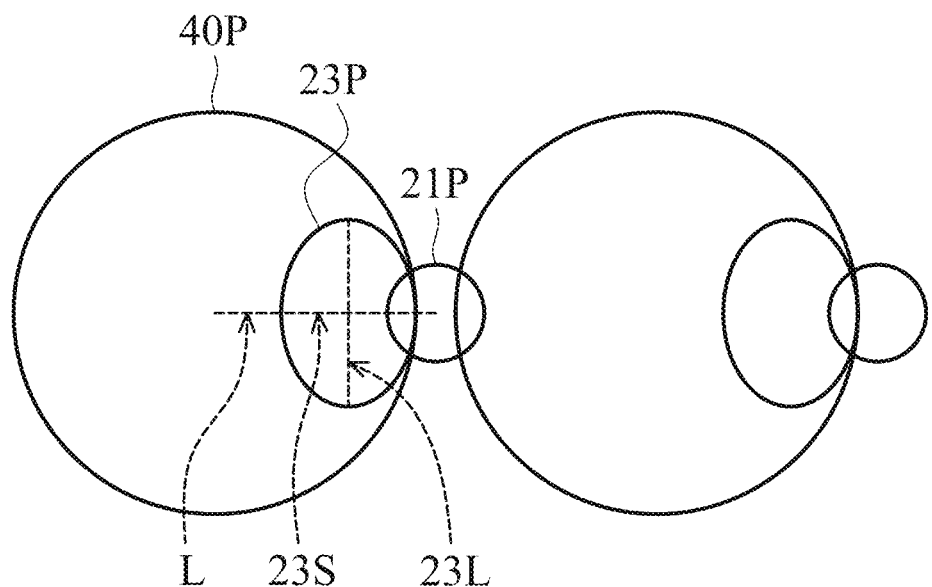
FIG. 2 is a schematic diagram illustrating an orthogonal projection of the first aperture, an orthogonal projection of the second aperture, and an orthogonal projection of the light-condensing structure on the bottom surface of the substrate according to one embodiment of the present disclosure.

FIG. 2 is a schematic diagram illustrating an orthogonal projection 21P of the first aperture 21A, an orthogonal projection 23P of the second aperture 23A, and an orthogonal projection 40P of the light-condensing structure 40 on the bottom surface 10B of the substrate 10 according to one embodiment of the present disclosure. Referring to FIG. 1 and FIG. 2, in some embodiments, the orthogonal projection 23P of the second aperture 23A on the bottom surface 10B of the substrate 10 has a long axis of symmetry 23L and a short axis of symmetry 23S perpendicular to the long axis of symmetry 23L. For example, the orthogonal projection 23P of the second aperture 23A on the bottom surface 10B of the substrate 10 is ellipsoidal as shown in FIG. 2, but the present disclosure is not limited thereto.

Moreover, in some embodiments, the short axis of symmetry 23S is parallel with the connecting line L of the center of the orthogonal projection 21P of the first aperture 21A on the bottom surface 10B of the substrate 10 and the center of the orthogonal projection 40P of the light-condensing structure 40 on the bottom surface 10B of the substrate 10. In more detail, the short axis of symmetry 23S of the orthogonal projection 23P of the second aperture 23A on the bottom surface 10B of the substrate 10 may overlap the connecting line L. In other words, the extension line of the short axis of symmetry 23S may pass through the center of the orthogonal projection 21P of the first aperture 21A on the bottom surface 10B of the substrate 10 and the center of the orthogonal projection 40P of the light-condensing structure 40 on the bottom surface 10B of the substrate 10.

As shown in FIG. 2, in some embodiments, the orthogonal projection 40P of the light-condensing structure 40 on the bottom surface 10B of the substrate 10 is circular, the orthogonal projection 23P of the second aperture 23A on the bottom surface 10B of the substrate 10 is ellipsoidal, and the orthogonal projection 21P of the first aperture 21A on the bottom surface 10B of the substrate 10 is circular. That is, the long axis of symmetry 23L is the major axis of the orthogonal projection 23P of the second aperture 23A and the short axis of symmetry 23S is the minor axis of the orthogonal projection 23P of the second aperture 23A, but the present disclosure is not limited thereto.

Figure 3:
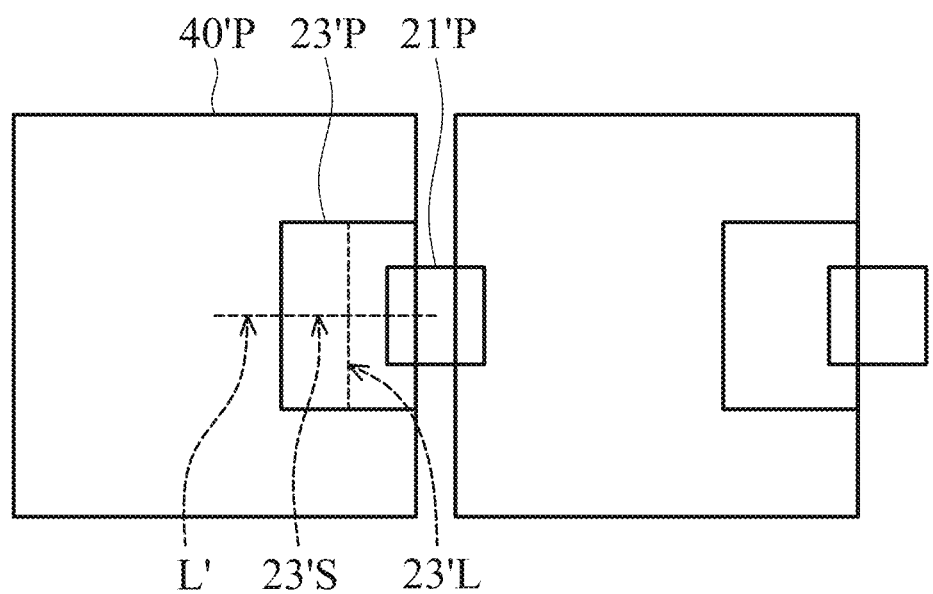
FIG. 3 is a schematic diagram illustrating an orthogonal projection of the first aperture, an orthogonal projection of the second aperture, and an orthogonal projection of the light-condensing structure on the bottom surface of the substrate according to another embodiment of the present disclosure.

FIG. 3 is a schematic diagram illustrating an orthogonal projection 21'P of the first aperture 21A, an orthogonal projection 23'P of the second aperture 23A, and an orthogonal projection 40'P of the light-condensing structure 40 on the bottom surface 10B of the substrate 10 according to another embodiment of the present disclosure. Similarly, Referring to FIG. 1 and FIG. 3, in some embodiments, the orthogonal projection 23'P of the second aperture 23A on the bottom surface 10B of the substrate 10 has a long axis of symmetry 23'L and a short axis of symmetry 23'S perpendicular to the long axis of symmetry 23'L.

As shown in FIG. 3, in some embodiments, the orthogonal projection 40'P of the light-condensing structure 40 on the bottom surface 10B of the substrate 10 is square-shaped, the orthogonal projection 23'P of the second aperture 23A on the bottom surface 10B of the substrate 10 is rectangular, and the orthogonal projection 21'P of the first aperture 21A on the bottom surface 10B of the substrate 10 is square-shaped, but the present disclosure is not limited thereto.

Figure 4:
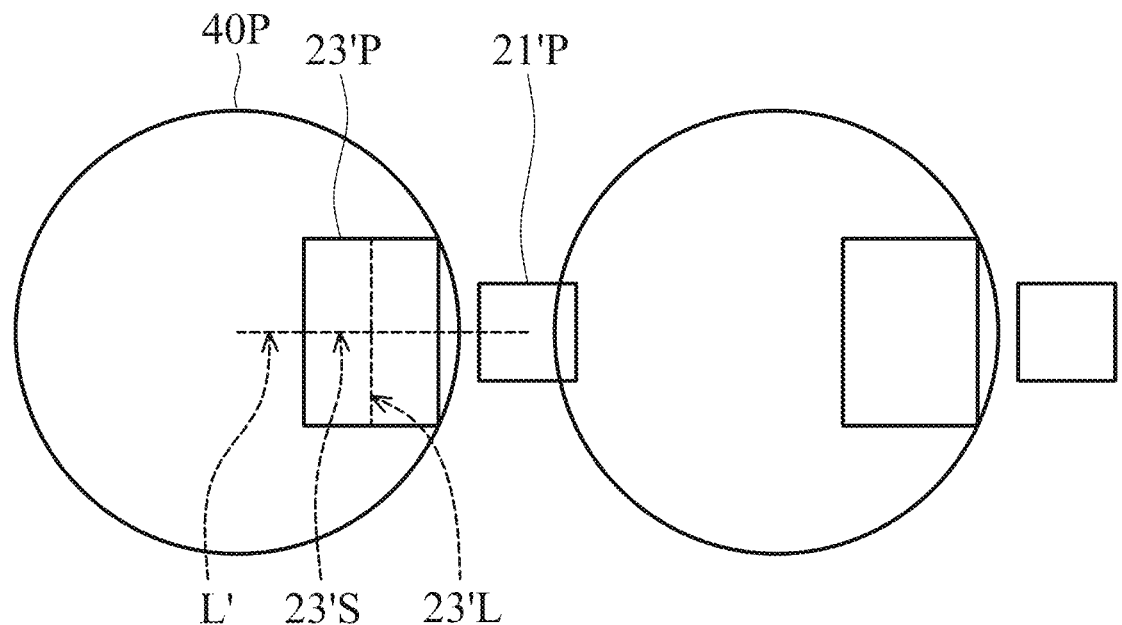
FIG. 4 is a schematic diagram illustrating an orthogonal projection of the first aperture, an orthogonal projection of the second aperture, and an orthogonal projection of the light-condensing structure on the bottom surface of the substrate according to another embodiment of the present disclosure.

Although the orthogonal projection of the light-condensing structure 40 on the bottom surface 10B of the substrate 10 has the same shape as the orthogonal projection of the first aperture 21A on the bottom surface 10B of the substrate 10, the present disclosure is not limited thereto. FIG. 4 is a schematic diagram illustrating an orthogonal projection 21'P of the first aperture 21A, an orthogonal projection 23'P of the second aperture 23A, and an orthogonal projection 40P of the light-condensing structure 40 on the bottom surface 10B of the substrate 10 according to another embodiment of the present disclosure.

As shown in FIG. 4, in some embodiments, the orthogonal projection 40P of the light-condensing structure 40 on the bottom surface 10B of the substrate 10 is circle, the orthogonal projection 23'P of the second aperture 23A on the bottom surface 10B of the substrate 10 is rectangular, and the orthogonal projection 21'P of the first aperture 21A on the bottom surface 10B of the substrate 10 is square-shaped, but the present disclosure is not limited thereto.

Figure 5:
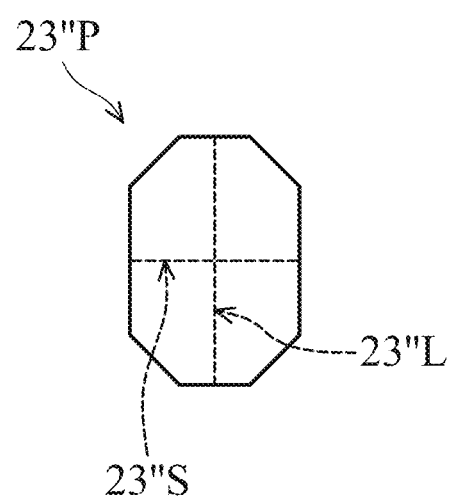
FIG. 5 is a schematic diagram illustrating an orthogonal projection of the second aperture on the bottom surface of the substrate according to one embodiment of the present disclosure.

In some other embodiments of the present disclosure, the second aperture 23A of the second light-shielding layer 23 in the semiconductor device 100 may have other shapes. FIG. 5 is a schematic diagram illustrating an orthogonal projection 23"P of the second aperture 23A on the bottom surface 10B of the substrate 10 according to one embodiment of the present disclosure. Similarly, Referring to FIG. 1 and FIG. 5, in some embodiments, the orthogonal projection 23"P of the second aperture 23A on the bottom surface 10B of the substrate 10 has a long axis of symmetry 23"L and a short axis of symmetry 23"S perpendicular to the long axis of symmetry 23"L.

As shown in FIG. 5, the orthogonal projection 23"P of the second aperture 23A on the bottom surface 10B of the substrate 10 is polygon-shaped, but the present disclosure is not limited thereto.

Since the second aperture 23A (or the orthogonal projection of the second aperture 23A on the bottom surface 10B of the substrate 10) of the second light-shielding layer 23 in the embodiments of the present disclosure has a long axis of symmetry and a short axis of symmetry perpendicular to the long axis of symmetry, it may be used for receiving/collecting inclined light and preventing crosstalk, thereby improving the quality of the image signal from the photoelectric conversion elements 12 of the semiconductor device 100.

Figure 6:
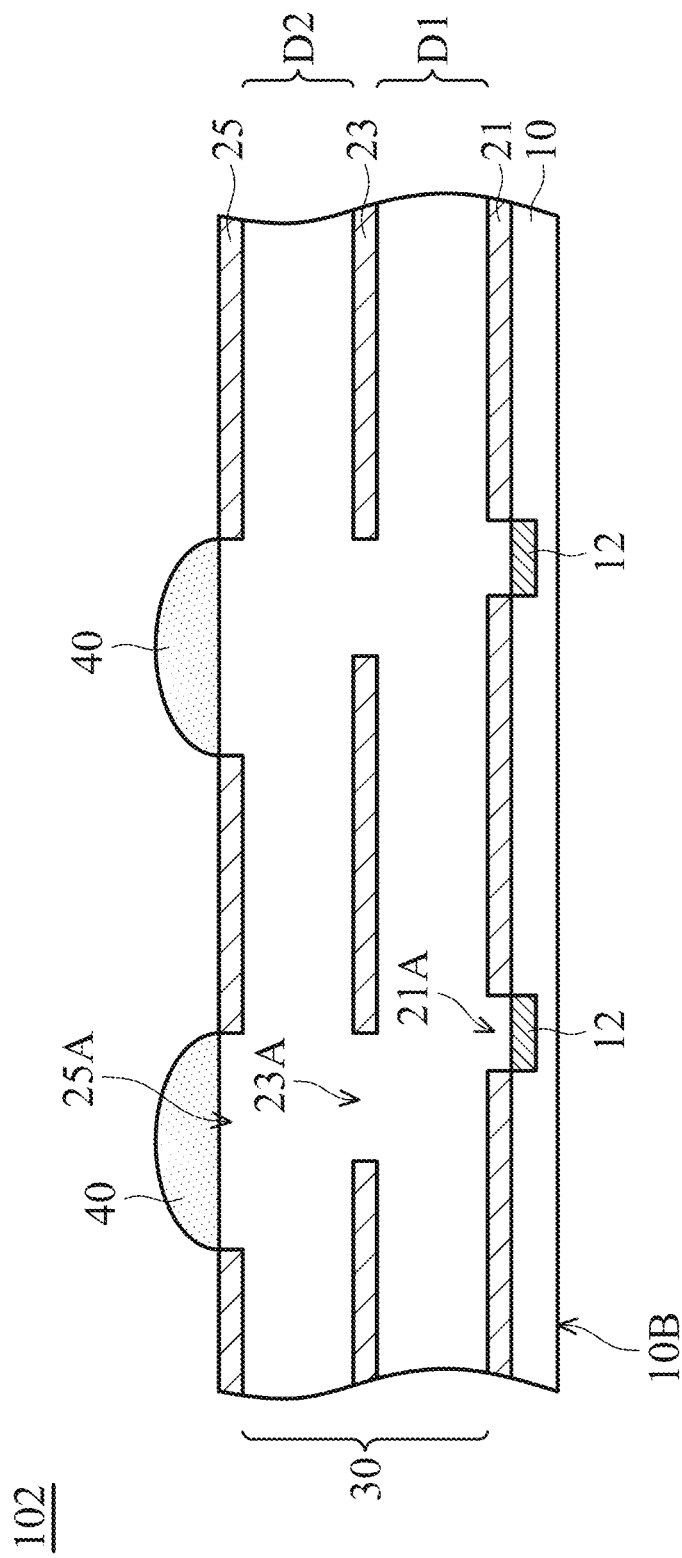
FIG. 6 is a partial cross-sectional view illustrating a semiconductor device according to another embodiment of the present disclosure.

FIG. 6 is a partial cross-sectional view illustrating a semiconductor device 102 according to another embodiment of the present disclosure. It should be noted that some components of the semiconductor device 102 may be omitted in FIG. 6, for the sake of brevity.

Referring to FIG. 6, the semiconductor device 102 may have similar structure to the semiconductor device 100 shown in FIG. 1. The difference is that the semiconductor device 102 shown in FIG. 6 may further include a third light-shielding layer 25 disposed on the light-transmitting layer 30. As shown in FIG. 6, the third light-shielding layer 25 may have a plurality of third apertures 25A that correspond to the second apertures 23A, the first apertures 21A, and photoelectric conversion elements 12.

In some embodiments, the material of the third light-shielding layer 25 may be similar to that of the second light-shielding layer 23, and the forming method of the third light-shielding layer 25 and the third apertures 25A may be similar to that of the second light-shielding layer 23 and the second apertures 23A as described above, and will not be repeated here.

As shown in FIG. 6, in some embodiments, the light-condensing structures 40 may cover the third apertures 25A of the third light-shielding layer 25. For example, the third aperture 25A may have the same shape as the light-condensing structure 40, but the present disclosure is not limited thereto.

In some embodiments, the distance D1 between the first light-shielding layer 21 and the second light-shielding layer 23 may be different from the distance D2 between the second light-shielding layer 23 and the third light-shielding layer 25, but the present disclosure is not limited thereto. In some other embodiments, the distance D1 between the first light-shielding layer 21 and the second light-shielding layer 23 may be the same as the distance D2 between the second light-shielding layer 23 and the third light-shielding layer 25, which may be adjusted depending on actual need.

Similarly, in the embodiment of FIG. 6, the second aperture 23A of the second light-shielding layer 23 in the semiconductor device 102 may have a long axis of symmetry and a short axis of symmetry perpendicular to the long axis of symmetry. In other words, the orthogonal projection of the second aperture 23A on the bottom surface 10B of the substrate 10 may be shown as the orthogonal projection 23P shown in FIG. 2, the orthogonal projection 23'P shown in FIG. 3 and FIG. 4, or the orthogonal projection 23"P shown in FIG. 5, but the present disclosure is not limited thereto.

In summary, since the aperture (or the orthogonal projection of the aperture on the bottom surface of the substrate) of the middle light-shielding layer (e.g., the second light-shielding layer 23) of the semiconductor device in the embodiments of the present disclosure has a long axis of symmetry and a short axis of symmetry perpendicular to the long axis of symmetry, it may be used for receiving/collecting inclined light and preventing crosstalk, thereby improving the quality of the image signal from the photoelectric conversion elements of the semiconductor device.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure. Therefore, the scope of protection should be determined through the claims. In addition, although some embodiments of the present disclosure are disclosed above, they are not intended to limit the scope of the present disclosure.

Reference throughout this specification to features, advantages, or similar language does not imply that all of the features and advantages that may be realized with the present disclosure should be or are in any single embodiment of the disclosure. Rather, language referring to the features and advantages is understood to mean that a specific feature, advantage, or characteristic described in connection with an embodiment is included in at least one embodiment of the present disclosure. Thus, discussions of the features and advantages, and similar language, throughout this specification may, but do not necessarily, refer to the same embodiment.

Furthermore, the described features, advantages, and characteristics of the disclosure may be combined in any suitable manner in one or more embodiments. One skilled in the relevant art will recognize, in light of the description herein, that the disclosure can be practiced without one or more of the specific features or advantages of a particular embodiment. In other instances, additional features and advantages may be recognized in certain embodiments that may not be present in all embodiments of the disclosure.

What is claimed is:

1. A semiconductor device, comprising:
    a substrate having a photoelectric conversion element;
    a first light-shielding layer disposed on the substrate and having a first aperture corresponding to the photoelectric conversion element;
    a light-transmitting layer disposed on the first light-shielding layer;
    at least one second light-shielding layer disposed in the light-transmitting layer and having a second aperture corresponding to the first aperture; and
    a light-condensing structure disposed on the light-transmitting layer and corresponding to the second aperture;
    wherein an orthogonal projection of the second aperture on a bottom surface of the substrate has a long axis of symmetry and a short axis of symmetry perpendicular to the long axis of symmetry, the short axis of symmetry is parallel with a connecting line of a center of an orthogonal projection of the first aperture on the bottom surface of the substrate and a center of an orthogonal projection of the light-condensing structure on the bottom surface of the substrate.

2. The semiconductor device as claimed in claim 1, wherein the short axis of symmetry overlaps the connecting line of the center of the orthogonal projection of the first aperture on the bottom surface of the substrate and the center of the orthogonal projection of the light-condensing structure on the bottom surface of the substrate.

3. The semiconductor device as claimed in claim 2, wherein the orthogonal projection of the light-condensing structure on the bottom surface of the substrate is circular.

4. The semiconductor device as claimed in claim 3, wherein the orthogonal projection of the second aperture on the bottom surface of the substrate is ellipsoidal.

5. The semiconductor device as claimed in claim 4, wherein the long axis of symmetry is a major axis of the orthogonal projection of the second aperture and the short axis of symmetry is a minor axis of the orthogonal projection of the second aperture.

6. The semiconductor device as claimed in claim 3, wherein the orthogonal projection of the second aperture on the bottom surface of the substrate is rectangular.

7. The semiconductor device as claimed in claim 2, wherein the orthogonal projection of the light-condensing structure on the bottom surface of the substrate is square-shaped.

8. The semiconductor device as claimed in claim 7, wherein the orthogonal projection of the second aperture on the bottom surface of the substrate is rectangular.

9. The semiconductor device as claimed in claim 1, wherein the orthogonal projection of the second aperture on the bottom surface of the substrate is polygon-shaped.

10. The semiconductor device as claimed in claim 1, further comprising:
    a third light-shielding layer disposed on the light-transmitting layer and having a third aperture corresponding to the second aperture.

11. The semiconductor device as claimed in claim 10, wherein the light-condensing structure covers the third aperture.

12. The semiconductor device as claimed in claim 11, wherein the third aperture has the same shape as the light-condensing structure.

13. The semiconductor device as claimed in claim 11, wherein a distance between the first light-shielding layer and the at least one second light-shielding layer is different from a distance between the at least one second light-shielding layer and the third light-shielding layer.

14. The semiconductor device as claimed in claim 1, wherein a material of the first light-shielding layer comprises a metal.

15. The semiconductor device as claimed in claim 1, wherein a material of the at least one second light-shielding layer comprises a photoresist, an ink, a molding compound, a solder mask, an epoxy resin, or a combination thereof.

16. The semiconductor device as claimed in claim 1, wherein the light-condensing structure comprises a micro-lens structure, a micro-pyramid structure, a micro-trapezoidal structure, or a gradient-index structure.

* * * * *